US009610411B2

(12) United States Patent
Clancy et al.

(10) Patent No.: US 9,610,411 B2
(45) Date of Patent: Apr. 4, 2017

(54) WIRE-EMBEDDED POLYMER-BODY NEEDLE

(71) Applicant: Cook Medical Technologies LLC, Bloomington, IN (US)

(72) Inventors: Michael S. Clancy, Limerick (IE); John Neilan, Co. Galway (IE); Darach McGrath, Co. Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 68 days.

(21) Appl. No.: 14/492,984

(22) Filed: Sep. 22, 2014

(65) Prior Publication Data
US 2015/0099995 A1    Apr. 9, 2015

Related U.S. Application Data

(60) Provisional application No. 61/886,334, filed on Oct. 3, 2013.

(51) Int. Cl.
| | |
|---|---|
| *A61B 5/00* | (2006.01) |
| *A61M 5/32* | (2006.01) |
| *A61B 10/02* | (2006.01) |
| *A61B 10/04* | (2006.01) |
| *A61M 5/158* | (2006.01) |
| *A61B 17/34* | (2006.01) |
| *A61B 90/00* | (2016.01) |

(52) U.S. Cl.
CPC ....... *A61M 5/3286* (2013.01); *A61B 10/0233* (2013.01); *A61B 10/04* (2013.01); *A61B 17/3478* (2013.01); *A61M 5/158* (2013.01); *A61B 2010/045* (2013.01); *A61B 2090/3925* (2016.02); *A61M 2205/0266* (2013.01)

(58) Field of Classification Search
CPC . A61B 10/02; A61B 10/0233; A61B 10/0275; A61B 10/04; A61B 2010/045; A61B 17/3478; A61B 2090/3925; A61M 5/158; A61M 5/3286; A61M 2205/0266
See application file for complete search history.

(56) References Cited

U.S. PATENT DOCUMENTS

| | | | |
|---|---|---|---|
| 5,092,848 A | 3/1992 | deCiutiis | |
| 5,897,537 A | * 4/1999 | Berg | A61M 25/0009 138/134 |

(Continued)

OTHER PUBLICATIONS

International Search Report for PCT/US2014/056793 dated Dec. 10, 2014; 10 pages.

*Primary Examiner* — Max Hindenburg
(74) *Attorney, Agent, or Firm* — Eric D. Babych; Brinks Gilson & Lione

(57) ABSTRACT

A medical needle including an elongate tubular body having an outer wall defining at least one longitudinal lumen is provided. The at least one longitudinal lumen may be configured to provide access for at least one of a wire guide, a therapeutic tool, a diagnostic tool, a medicament, and/or contrast fluid. The body may be configured with sufficient length and flexibility to be extended out of and operated through a working channel of a surgical endoscope. The body further includes one or more wires embedded in, and secured substantially immovably relative to, the outer wall. A distal end of the body includes a needle tip configured with at least one sharpened surface configured to penetrate into body tissue.

16 Claims, 3 Drawing Sheets

(56) References Cited

U.S. PATENT DOCUMENTS

| | | | |
|---|---|---|---|
| 5,935,108 A | 8/1999 | Katoh et al. | |
| 6,554,794 B1* | 4/2003 | Mueller | A61B 17/3478 |
| | | | 604/528 |
| 6,855,124 B1 | 2/2005 | Gonzalez et al. | |
| 8,202,258 B2 | 6/2012 | Zambaux et al. | |
| 8,979,803 B2* | 3/2015 | Darr | A61B 10/0275 |
| | | | 604/164.1 |
| 2002/0143291 A1 | 10/2002 | Slater | |
| 2005/0124977 A1 | 6/2005 | Gonzalez et al. | |
| 2010/0228276 A1 | 9/2010 | Breznock | |
| 2013/0006144 A1 | 1/2013 | Clancy et al. | |
| 2013/0123620 A1 | 5/2013 | Tekulve et al. | |

* cited by examiner

WIRE-EMBEDDED POLYMER-BODY NEEDLE

CROSS-REFERENCE TO RELATED APPLICATIONS

The present application claims the benefit of U.S. Provisional Patent Application No. 61/886,334, filed Oct. 3, 2013, the entire contents of which are herein incorporated by reference in their entirety.

TECHNICAL FIELD

Embodiments disclosed herein generally relate to medical devices. More particularly, the disclosed embodiments relate to biopsy and access needles comprising polymer bodies having one or more wires embedded therein.

BACKGROUND

The development of minimally invasive methods and devices over recent years has revolutionized the practice of medicine. These methods and devices allow medical professionals to perform a wide variety of procedures while minimizing trauma to the patient. Access needles are used in connection with certain minimally invasive medical procedures. These needles may include a tubular cannula body that can form a conduit between a target site within the body of a patient and a location outside of the patient's body. This conduit can subsequently be used by a medical professional for performing certain procedures in connection with the target site or for running a wire guide therethrough.

An access needle may include a stylet in the lumen of its cannula to avoid inadvertent sample collection at the distal end of the cannula, to provide a sharp tip capable of making a puncture, and to provide some reinforcement to the cannula as it travels to the target site within the body. After the distal end of the needle arrives at its target location within the body, the stylet may be withdrawn, thereby clearing a space through the cannula lumen where, for example, a wire guide may be placed. A medical professional performing such a procedure must be able to determine the exact location of the distal end of the cannula to be sure that it has arrived at the precise target site within the body of the patient.

One method useful for determining the location of the distal end of the cannula within the patient's body is carried out using endoscopic ultrasound (EUS). EUS provides a medical professional with the ability to visualize the location of the distal end of the needle within the patient's body without requiring an open incision, use of large-bore needles, or percutaneous trocars. If this method is used for location purposes, the access needle may comprise an echogenic tip at its distal end. Ideally, EUS can then be used to determine the location of the echogenic tip. However, EUS technology is not always capable of providing the medical professional with precise location data. Thus, it could be advantageous to couple EUS with a different form of location technology either to supplement the EUS data or provide location data in the event that EUS is unsuccessful.

In this regard, fluoroscopy may be used as an additional method to determine the location of the distal end of a needle within a patient's body. In one aspect, fluoroscopy may be used to detect a dye or contrast fluid that has been placed within the patient's body. Specifically, x-rays are emitted through the body of the patient to determine the exact location of the contrast fluid. The resulting image may be transmitted to a monitor and a medical professional carrying out the procedure can then determine if the distal end of the needle is at the target site.

Existing biopsy needles are generally manufactured using a cannula made from stainless steel, nitinol, cobalt chromium, or other metal alloys. Using a needle made from such materials to take cytology or histology samples can have various negative effects. For example, oxides may form on the metal surface and the chemicals used in the cannula manufacturing process can remain on the inner surfaces of the needle. The contamination can be transferred from the needle lumen or stylet surface during sample collection and thus, the sample may become contaminated or the contamination may be passed into the patient.

Also, certain metal needles will take an induced shape set (bending) as the needle is advanced from the distal tip of the scope into the target tissue. The induced shape set makes subsequent needle passes to different areas of the anatomy difficult as the needle will not follow a straight line. The user may have to manually straighten the distal end of the needle after each needle pass or use more expensive metals to prevent shape set occurrence.

Additionally, if the needle is supplied with a metal stylet, high friction can occur between the stylet surface and the needle lumen. The metal-on-metal friction will lead to increased stylet removal forces when the device is in a difficult to reach anatomical location. Finally, injection of therapeutics through metal needles can cause contamination from the needle to be transferred into the patient with the therapeutic agents.

Polymer-body needles are known in the art (e.g., U.S. Pat. No. 5,092,848 to deCiutiis), but improved configurations are needed that provide desirable pushability, trackability, and columnar strength—particularly during use in gastrointestinal endoscopy procedures (including, for example, endoscopic retrograde cholangiography procedures).

BRIEF SUMMARY

The present disclosure relates to medical needles and methods for using medical needles. In one aspect, a medical needle is provided, wherein the medical needle comprises an elongate tubular polymer body including an outer wall defining at least one longitudinal lumen. The needle also includes a plurality of wires embedded in and secured substantially immovably relative to the outer wall. Also, the needle comprises a needle tip configured with at least one sharpened surface configured to penetrate into body tissue. At least one of the plurality of wires is secured directly to the needle tip. The polymer body is configured with sufficient length and flexibility to be extended out of and operated through a working channel of a surgical endoscope.

In another aspect, a medical needle is provided, wherein the medical needle comprises an elongate tubular body including an outer wall defining at least one longitudinal lumen. The needle also includes a plurality of longitudinal channels disposed in the outer wall of the elongate tubular body. Further, a plurality of longitudinal, non-overlapping wires are embedded in, and secured substantially immovably relative to, the outer wall. Each of the plurality of wires is disposed in a separate channel of the plurality of channels. The needle also comprises a metal needle tip configured with at least one sharpened surface configured to penetrate into body tissue. At least one of the plurality of wires is secured directly to the metal needle tip. Finally, the medical needle comprises features to enhance its echogenicity.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION

Figure 1:
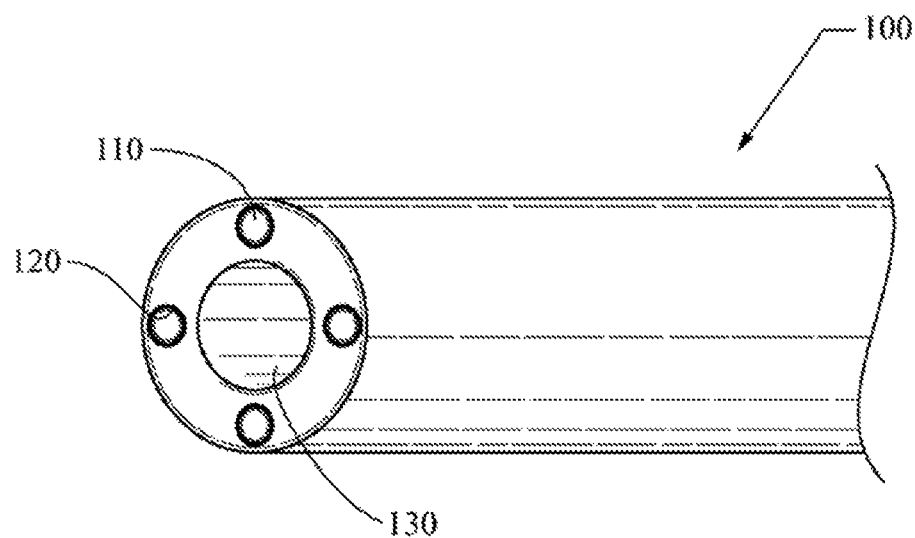
FIG. 1 shows a cross-sectional side view of an aspect of the presently disclosed medical needle.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The present disclosure provides needles comprising a polymer body, which addresses the problems noted above with respect to metal needles. Furthermore, the present disclosure provides needles comprising a polymer body and including a distal metal needle tip, which provides the advantages well-known in the art for metal needles (e.g., tissue penetration for access and/or sample-gathering).

Prior art needles comprising polymer bodies are prone to kinking and/or may lack desirable column strength for advancement into/through challenging locations and/or hard lesions. Therefore, the present disclosure addresses those problems and presents a novel design by providing needle embodiments with a metal distal tip and a wire-embedded polymer body.

The use of a polymer body comprising one or more longitudinal wires embedded therein, and substantially securely attached thereto, represents an optimum solution to the problems associated with prior art needles comprising polymeric bodies. The embedded longitudinal wire(s) prevents the plastic cannula from kinking in difficult to reach anatomical locations and provides additional columnar strength as the plastic needle is advanced through or into hard lesions or tissue.

In one aspect, the present disclosure provides a medical needle comprising an elongate tubular polymer body including an outer wall defining at least one longitudinal lumen. The at least one longitudinal lumen may be configured to provide access for at least one of a wire guide, a therapeutic tool, a diagnostic tool, a medicament, and/or contrast fluid. The body may be configured with sufficient length and flexibility to be extended out of and operated through a working channel of a surgical endoscope.

The polymer body may further comprise a plurality of longitudinal, non-overlapping, wires embedded in and secured substantially immovably or immovably relative to the outer wall. A metal needle tip configured with at least one sharpened surface configured to penetrate into body tissue is attached at a distal end of the polymer body. To facilitate attachment of the metal needle tip, in certain aspects, at least one of the plurality of wires is secured directly to the metal needle tip.

The polymer body of the presently disclosed medical needles is not specifically limited to any particular polymer and may be made from a variety of known monomers. The polymer body may be made from numerous different types of plastics. In one aspect, the polymer body may be made from nylon. In another aspect, the polymer body may be made from polyetheretherketone (PEEK). In an additional aspect, the polymer body may include nylon and/or PEEK. In further aspects, the polymer body may comprise polyimide, polyethylene, polyurethane, and any other polymer that can be extruded. The body of the presently disclosed needles is not limited to a particular type of polymer.

In certain aspects, the longitudinal, non-overlapping, wires embedded in the polymer body are immovably secured, or substantially immovably secured, relative to the outer wall of the polymer body. Such a configuration would be opposite from a configuration wherein the wires are slidably disposed in the polymer body, such that when pushing or pulling on an end of the wire, the wire would freely move through a channel in the polymer body. Instead, with a wire immovably secured, or substantially immovably secured, in a channel of the polymer body, when pushing or pulling on an end of the wire, the wire would not move or would be substantially immobile relative to the polymer body.

In certain aspects, a channel may be formed in the polymer body and the channel would have a diameter substantially equal to the diameter of the wire. Thus, since the diameter of the wire and the diameter of the channel would be substantially equal, the friction forces would be high enough to prevent movement of the wire in the channel. In some aspects, adhesive may also be applied to the wire, channel, or both, such that when the wire is placed into the channel, the adhesive would secure the wire in place such that movement of the wire in the channel would be restricted.

The polymer bodies disclosed herein may have any number of wires running therethrough. For example, FIG. 1 shows a polymer body (100) having four wires (110) running therethrough. The wires do not extend into the lumen (130) of the body (100) but instead are placed in channels (120) that have been formed in the wall of the polymer body (100). Although FIG. 1 depicts a polymer body comprising four wires, in other aspects, the polymer body may comprise one, two, three, five, six, seven, eight, nine, ten, or more, longitudinal wires.

In certain aspects of this disclosure, it is advantageous to provide these wires as longitudinal wires. That is, the wire is provided in the polymer body such that its longitudinal axis is parallel with the longitudinal axis of the polymer body. A polymer body comprising one or more longitudinal wires provides various benefits to the medical needle, such as imparting it with greater pushability and columnar strength when, for example, piercing a lesion in the body.

Certain problems associated with needles comprising polymer bodies have been previously described and providing a polymer body having wires placed in, for example, a braided or helical configuration, may not be able to overcome these problems. Such configurations may have a tendency to stretch or compress, for example.

The longitudinal wires may be circumferentially spaced in the polymer body in any configuration; symmetric or asymmetric. For example, in FIG. 1, the wires are substantially symmetrically circumferentially spaced at about 90 degree intervals. In other aspects, if five wires were included in the polymer body, the wires could be symmetrically spaced at about 72 degree intervals. However, asymmetric placement of the wires is also contemplated by the present disclosure.

The wires provided in the polymer body can be made from many different metals known in the art, such as stainless steel, nitinol, cobalt chromium, etc. In certain aspects, the wires comprise a shape-memory alloy/memory metal. A memory metal is an alloy that "remembers" its original, cold-forged shape. Illustrative examples of memory metals are copper-aluminium-nickel and nickel-titanium (NiTi) alloys. Memory metals can also be formed by alloying zinc, copper, gold and/or iron. In some aspects, the memory metal is configured to orient a length of the needle along a desired straight or curved line.

Figure 4:
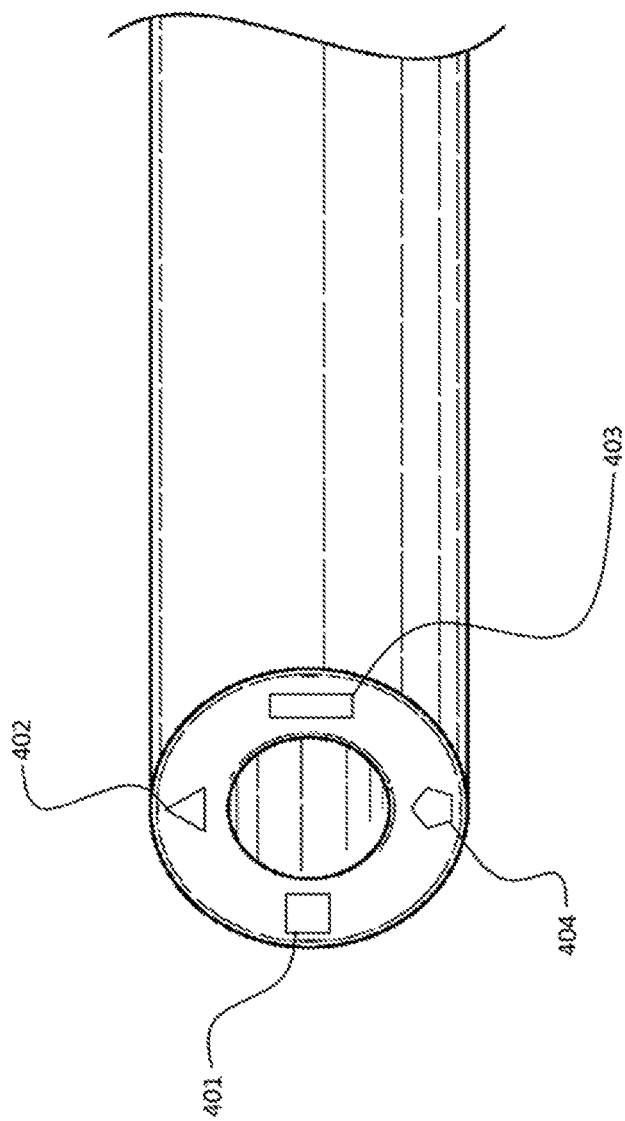
FIG. 4 shows another embodiment of the presently disclosed medical needle illustrating different wire profile shapes.

The thickness of each wire can vary depending upon the desired characteristics of the wire and the diameter of any of the presently disclosed wires is not limited. If a more flexible polymer body is desired, one may wish to create wires having relatively smaller diameters. If high pushability and columnar strength are desired, one may wish to create wires having relatively larger diameters. Also, as shown in FIG. 4, the cross-sectional shape of each wire can vary. For example, in some aspects, one or more of the plurality of wires may comprise a circular cross-section. Alternatively, one or more of the plurality of wires may comprise a non-circular cross-section, such as a square 401, triangle 402, rectangle 403, pentagon 404, hexagon, octagon, etc., cross-section.

Along the same lines, the presently disclosed polymer body can be made to accommodate any desired needle size/gauge. In some aspects, the polymer body can be used with a needle having a gauge from about 19 to about 25. For example, in one aspect, the polymer body may be used with a 19-gauge needle. In another aspect, the polymer body may be used with a 21-gauge needle or a 23-gauge needle and, in an additional aspect, the polymer body may be used with a 25-gauge needle.

Attaching a metal needle tip to a polymeric cannula can be highly problematic for a number of different reasons. For example, if a metal tip is attached to the polymeric body by an adhesive, the tip could become separated from the body if a high degree of force is required to withdraw the needle from an anatomical location in the patient's body. However, such problems are overcome due to the incorporation of the wires in the presently disclosed polymer body.

For example, in certain aspects, one or more of the wires can be welded or soldered to the metal needle tip. In some aspects, each of the plurality of wires is secured to the metal needle tip. In additional aspects, a distal portion of the polymer body overlaps a proximal portion of the metal needle tip. In still further aspects, the metal needle tip is continuous in construction with at least one of the plurality of wires.

Figure 2:
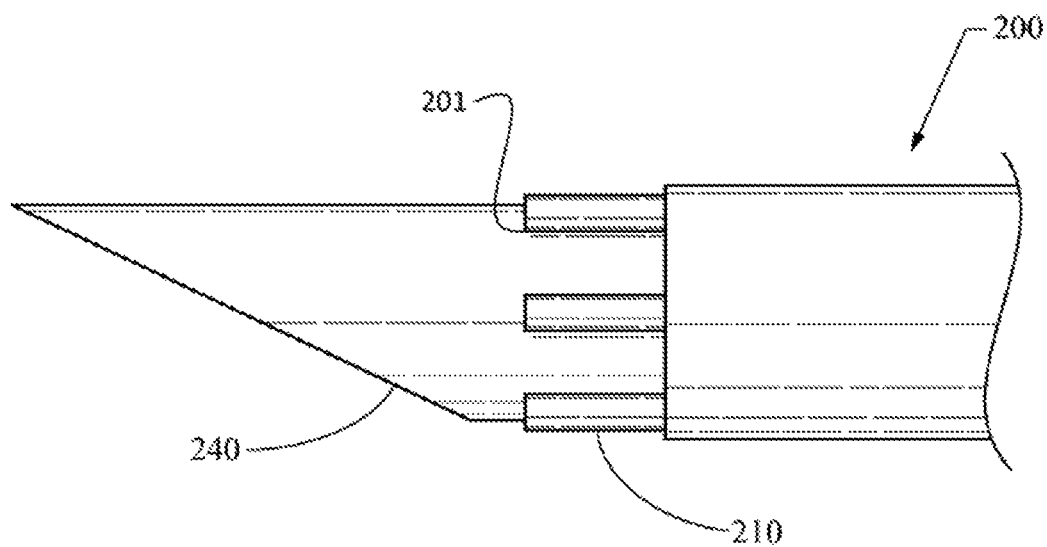
FIG. 2 shows a partial transverse sectional view of an aspect of the presently disclosed medical needle.

With respect to FIG. 2, one or more of the wires (210) may extend past the distal end of the polymer body (200) and the extended portion of the one or more wires (210) can be welded or soldered to the metal needle tip (240) at interface 201. Alternatively, the polymer body (200) may be formed with the plurality of wires (210) flush with the distal end of the polymer body (200) and then a portion of the distal end of the polymer body may be removed or peeled back so as to expose a distal end of the plurality of wires. One or more of the exposed wires (210) can then be welded or soldered to the metal needle tip (240) at interface 201. The metal needle tip (240) could also be bonded to the distal end of the polymer body or a heat-shrink material could be used to join the distal end of the polymer body to the proximal end of the metal needle tip. In alternate aspects where a metal needle tip is not included, the distal end of the polymer body could be ground into a bevel point and the plurality of wires would offer additional support to the formed tip.

In certain aspects, the metal needle tip can be made from any of the metals disclosed herein, or any other metal known in the art for fabricating metal needle tips. Further, the metal needle tip may comprise a beveled distal end and a side-opening configured for biopsy sample acquisition. Moreover, the outer diameter of the metal needle tip can be selected based upon the intended use of the medical needle. In some aspects, the outer diameter of the metal needle tip may be smaller or larger than the outer diameter of the polymer body. In other aspects, the outer diameter of the metal needle tip is substantially the same as the outer diameter of the polymer body.

Not only are the presently disclosed medical needles suitable for collection of tissue, in some aspects, the presently disclosed medical needles can be adapted for use with medical access needles. Access needles are used to place wire guides into, for example, cysts or bile ducts. The access needle is advanced into the target area using a sharp stylet tip, the stylet is then removed, and a wire guide is advanced through the needle lumen and into the target area. For this procedure, using a needle cannula incorporating the presently disclosed plurality of wires would allow a wire guide to be advanced without damage occurring to the outer surface of the wire guide, which often times occurs when a metal body cannula is used. The plurality of wires in the polymer body would provide the desired flexibility, pushability, and kink resistance properties.

In certain aspects, the metal needle tip and/or distal end of the polymer body may include surface features configured to enhance echogenicity, thereby providing an improved ability to navigate the medical needle during an EUS procedure. The surface features can comprise dimples on an exterior surface of the polymer body and/or needle tip but may alternatively be embodied as grooves or other regular or irregular features on an external or internal surface of the polymer body and/or needle tip. Embedded echogenic features such as bubbles, voids, or pieces of echo-contrasting materials may also be used within the scope of the present disclosure. Those of skill in the art will appreciate that many currently-known and/or future-developed echogenicity-enhancing means may be used within the scope of the present disclosure. In certain aspects, the echogenicity-enhancing features are disposed at a specified predetermined distance from the distal tip of the medical needle. Also, a stylet disposed in the needle lumen may include echogenicity-enhancing features instead of, or in addition to, those that may be disposed on the polymer body and/or needle tip.

As used herein, the terms echogenic and echogenicity-enhancing are used to refer to structural features that increase the reflectivity of ultrasound waves used during ultrasound visualization of a device, with the increase being over the typical ultrasound reflectivity/visualizability of a device lacking the features described.

The medical needle disclosed herein may be scaled and configured for use in fine-needle aspiration (FNA) procedures, fine-needle biopsy (FNB) procedures, other tissue-collection procedures, or it can be used as an access needle for placement of a wire guide. In any of these methods, the medical needle may include a handle, where the proximal end of the cannula is attached to the handle, and the medical needle may further comprise a sheath. The sheath may be constructed as a protective sheath configured to cover the needle while it is being advanced through an endoscope working channel, which sheath will protect both the needle and the working channel from contact that could damage either or both.

In one method disclosed herein, a target site within the body of a patient is visualized with an ultrasound endoscope. The presently disclosed medical needle comprising a stylet can be inserted into the ultrasound endoscope and attached to the scope. The handle of the needle can be advanced to puncture the distal end of the cannula/stylet assembly into the target site within the body of the patient. Once confirmation is received that the distal end of the cannula is at the correct location, the stylet may be removed.

Upon removal of the stylet, the cannula will be left in place with its distal end at the target site. The next steps of the method depend upon the needs of the medical professional and the patient. For example, a syringe can be connected to the handle of the needle to aspirate fluid from the target location. As an additional illustrative example, a wire guide can be passed through the cannula lumen into the target site within the patient's body. The handle of the access needle can then be retracted to bring the needle back into the sheath which surrounds the cannula. The device can then be removed from the endoscope, leaving the wire guide in place for further access to the target site.

Figure 3:
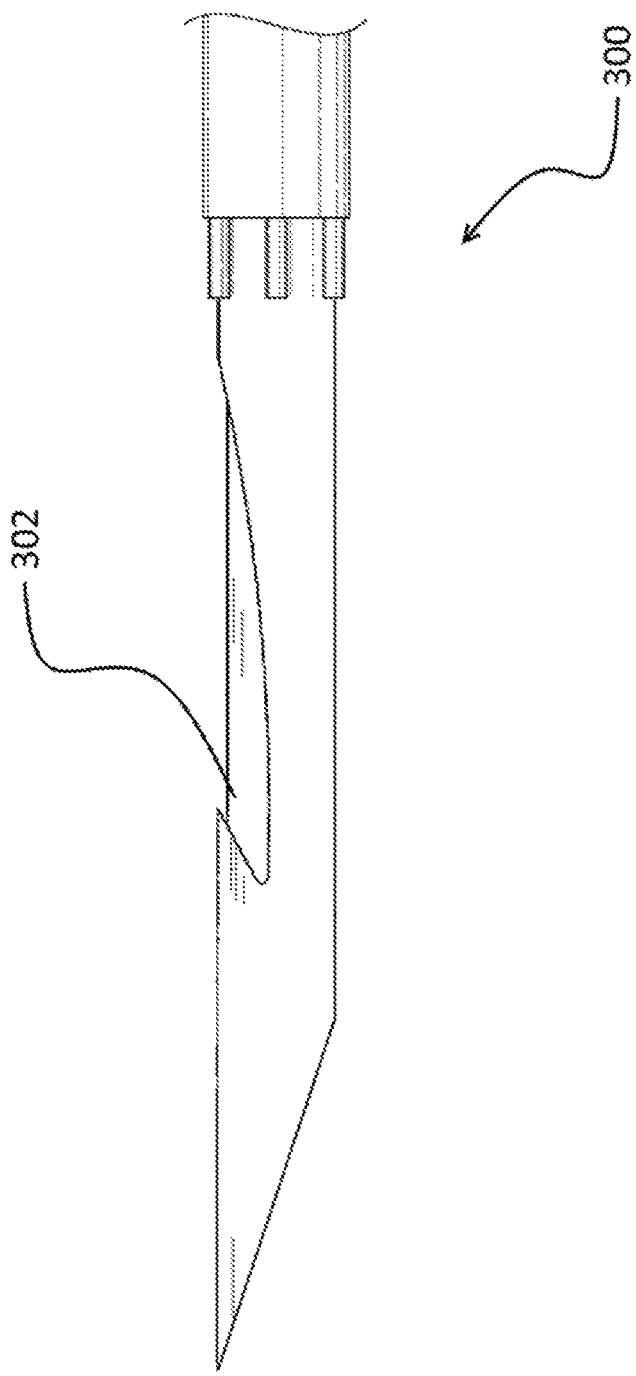
FIG. 3 shows a side-view of another embodiment of the presently disclosed medical needle.

In an additional method, tissue collection may be carried out using any aspect of the medical needle described herein. In one aspect shown in FIG. 3, the needle cannula (300), with a stylet disposed therein, may be directed via the working channel of a surgical visualization device (e.g., an EUS duodenoscope) into a target site to be sampled (e.g., a suspected tumor mass in the head of a patient's pancreas). The needle cannula (300) may comprise a notch (302) or cutting lip near its distal end (see, for example, WO 2011/126963, titled Endoscopic Ultrasound-Guided Biopsy Needle, the contents of which are incorporated into the present application in their entirety). The stylet may be withdrawn and suction applied to the needle cannula lumen. One or more of suction, rotary manipulation, and/or longitudinal manipulation of the needle cannula (300) will excise (e.g., via the cutting lip) and capture tissue, which preferably will include sufficiently intact samples for histology, from the target site through the notch (302) and/or distal end of the cannula into the cannula lumen.

The presently disclosed invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

As used in this specification, the terms "proximal" and "distal" should be understood as being in the terms of a physician or other person operating a medical device or on a patient. Hence, the term "distal means the direction or portion of the device that is farthest from the physician or other person and the term "proximal" means the portion of the device that is nearest to the physician or other person.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting.

Further, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A medical needle, comprising:
    an elongate tubular polymer body including an outer wall defining at least one longitudinal lumen;
    a plurality of wires embedded in and secured relative to the outer wall; and
    a needle tip configured with at least one sharpened surface configured to penetrate into body tissue;
    wherein at least one of the plurality of wires is secured directly to the needle tip; and
    wherein the polymer body is configured to be extended out of and operated through a working channel of a surgical endoscope.

2. The needle of claim 1, wherein the polymer body comprises nylon, polyetheretherketone (PEEK), or a combination thereof.

3. The needle of claim 1, wherein each of the plurality of wires is secured directly to the needle tip.

4. The needle of claim 1, wherein the needle tip is configured for collection of tissue.

5. The needle of claim 4, wherein the needle tip comprises a beveled distal end and a side-opening configured for biopsy sample acquisition.

6. The needle of claim 1, wherein at least one of the plurality of wires is exposed for some length outside the polymer body.

7. The needle of claim 1, wherein a distal portion of the polymer body overlaps a proximal portion of the needle tip.

8. The needle of claim 1, wherein at least one of the plurality of wires includes a memory metal.

9. The needle of claim 8, wherein the memory metal is configured to orient a length of the needle along a desired straight or curved line.

10. The needle of claim 1, wherein the needle tip comprises a metal.

11. The needle of claim 10, wherein at least one of the plurality of wires is welded to the needle tip.

12. The needle of claim 1, wherein an outer diameter of the needle tip is the same as an outer diameter of the polymer body.

13. The needle of claim 1, wherein at least one of the plurality of wires comprises a non-circular cross-section.

14. The needle of claim 1, wherein the plurality of wires comprises longitudinal, non-overlapping wires.

15. A medical needle, comprising:
- an elongate tubular body including an outer wall defining at least one longitudinal lumen;
- a plurality of longitudinal channels disposed in the outer wall of the elongate tubular body;
- a plurality of longitudinal, non-overlapping wires embedded in and secured relative to the outer wall, wherein each of the plurality of wires is disposed in a separate channel of the plurality of channels; and
- a metal needle tip configured with at least one sharpened surface configured to penetrate into body tissue;
- wherein at least one of the plurality of wires is secured directly to the metal needle tip and further wherein the medical needle comprises features to enhance echogenicity.

16. The needle of claim 15, wherein the elongate tubular body comprises a polymer, an outer diameter of each of the plurality of wires is identical to an inner diameter of each of the plurality of channels, and wherein a distal end of at least one of the plurality of wires is welded to a proximal end of the metal need tip.

* * * * *